(12) United States Patent
Vermandel et al.

(10) Patent No.: US 11,135,443 B2
(45) Date of Patent: Oct. 5, 2021

(54) SYSTEM FOR TREATMENT BY PHOTODYNAMIC THERAPY OF A CAVITY OF A PATIENT'S BODY AND METHOD FOR PREPARATION OF SUCH SYSTEM

(71) Applicants: INSERM (Institut National de la Sante et de la Recherche Medicale), Paris (FR); Universite de Lille, Lille (FR); Centre Hospitalier Regional et Universitaire de Lille (CHRU), Lille (FR)

(72) Inventors: Maximilien Vermandel, Lille (FR); Clement Dupont, Lille (FR); Nicolas Reyns, Lille (FR); Pascal Deleporte, Lille (FR); Serge Mordon, Lille (FR); Nacim Betrouni, Lille (FR)

(73) Assignees: INSERM (Institut National de la Santé et de la Recherche Médicale), Paris (FR); Université de Lille, Lille (FR); Centre Hospitalier Regional et Universitaire de Lille (CHRU), Lille (FR)

( * ) Notice: Subject to any disclaimer, the term of this patent is extended or adjusted under 35 U.S.C. 154(b) by 350 days.

(21) Appl. No.: 16/086,228

(22) PCT Filed: Mar. 24, 2017

(86) PCT No.: PCT/EP2017/057111
§ 371 (c)(1),
(2) Date: Sep. 18, 2018

(87) PCT Pub. No.: WO2017/162869
PCT Pub. Date: Sep. 28, 2017

(65) Prior Publication Data
US 2020/0289840 A1    Sep. 17, 2020

(30) Foreign Application Priority Data
Mar. 25, 2016 (EP) .................................. 16305347

(51) Int. Cl.
*A61N 5/06* (2006.01)
*A61N 5/067* (2006.01)

(52) U.S. Cl.
CPC ........... *A61N 5/0603* (2013.01); *A61N 5/062* (2013.01); *A61N 2005/063* (2013.01); *A61N 2005/067* (2013.01); *A61N 2005/0627* (2013.01)

(58) Field of Classification Search
CPC ......... A61N 5/0603; A61N 5/06; A61B 18/02
See application file for complete search history.

(56) References Cited

U.S. PATENT DOCUMENTS 5,125,925 A     6/1992  Lundahl
2002/0087206 A1* 7/2002 Hirschberg .......... A61N 5/0601
                                                    607/89
(Continued)

FOREIGN PATENT DOCUMENTS

WO      2014/145179 A1    9/2014
WO   WO-2014145179 A1 *   9/2014  ........... A61N 5/0601

OTHER PUBLICATIONS

DeLaney et al.; "A Light-Diffusing Device for Intraoperative Photodynamic Therapy in the Peritoneal or Pleural Cavity"; Journal of Clinical Laser Medicine & Surgery, Oct. 1, 1991, pp. 361-364.
(Continued)

*Primary Examiner* — Allen Porter
*Assistant Examiner* — Skylar Lindsey Christianson
(74) *Attorney, Agent, or Firm* — W & C IP

(57) ABSTRACT

System (1) for treatment by photodynamic therapy comprising an illuminating member (6) which comprises: —a core (35) carrying a light emitting surface (37), and —a hollow
(Continued)

Figure 1:
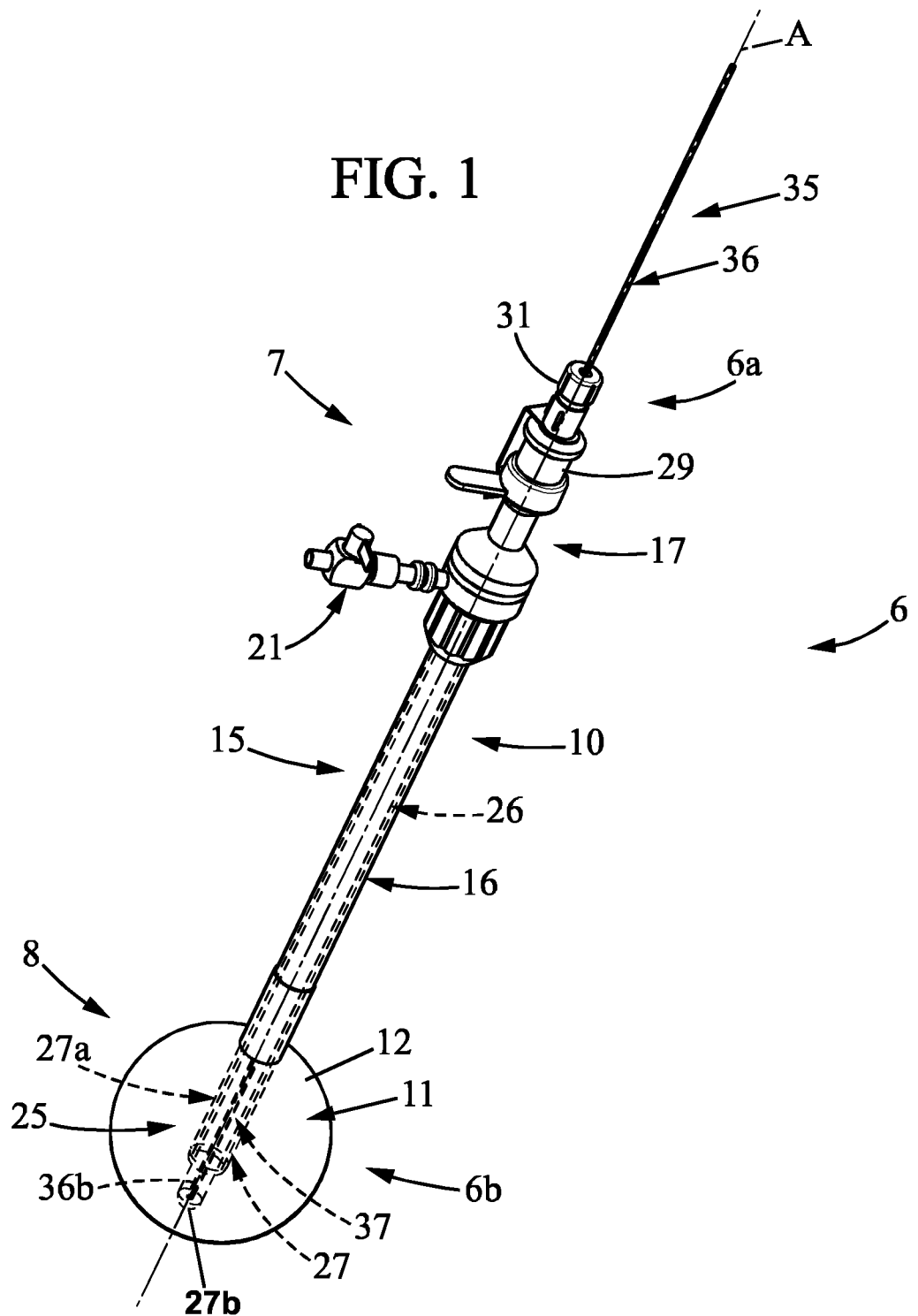

sheath (10) adapted to receive the core (35) with the light emitting surface (37) arranged within a balloon (11), the balloon (11) comprising a wall (12) which has an inner surface delimiting an internal space, and an outer surface, the wall (12) being flexible, wherein the internal space of the balloon (11) has a variable capacity, the wall (12) of the balloon (11) being elastically extendible and the balloon (11) presenting a plurality of inflated states in each of which the internal space is filled with a volume of light diffusing solution, and wherein the system further comprises a support provided with a transfer function relating the volume of light diffusing solution of each inflated state with at least one of a corresponding distribution of light power at the outer surface of the wall (12) of the balloon (11) and a corresponding time of illumination for providing a determined dose of light energy.

10 Claims, 4 Drawing Sheets

(56) References Cited

U.S. PATENT DOCUMENTS

2015/0190619 A1* 7/2015 Rocha-Singh .......... A61F 7/007
 604/509
2016/0287894 A1* 10/2016 Arai ....................... A61N 5/062

OTHER PUBLICATIONS

Lyons et al.; "The effects of PDT in primary malignant brain tumours could be improved by intraoperative radiotherapy"; Photodiagnosis and Photodynamic Therapy, vol. 9, No. 1, Dec. 1, 2011, pp. 40-45.

* cited by examiner

SYSTEM FOR TREATMENT BY PHOTODYNAMIC THERAPY OF A CAVITY OF A PATIENT'S BODY AND METHOD FOR PREPARATION OF SUCH SYSTEM

The invention relates to a system for treatment by photodynamic therapy of a cavity of a patient's body and to a method for preparation of such system.

Although not limited thereto, the invention finds particular application in neurosurgery and especially in surgical resection of a glioblastoma.

A glioblastoma is the most frequent malignant primitive cerebral tumor for an adult, with an incidence in France of 4/100,000. It is however considered as a rare disease. With a conventional treatment involving in particular surgery and radio-chemotherapy, the survival median is 14.5 months. The invasive nature of the glioblastoma explains in part its unavoidable recurrence. In spite of a seemingly complete macroscopic removal of a tumour even seemingly confirmed by medical imagery, there are always some invisible tumorous cells which remain after surgery. Those tumorous cells infiltrated in adjacent healthy tissues are insufficiently treated by a supplemental radio-chemotherapy. Recurrences then occur mainly initially at tumorous edges. It has been shown in numerous studies that the quality of the surgical resection is a major prognostic factor.

Hence, optimization of a local control of the quality of the surgical resection is a significant challenge to improve survival without progression of the tumor and thereby to improve the global survival.

With respect to such optimization, association with photodynamic therapy (PDT) delivered to the edges of the surgical resection has been considered. Photodynamic therapy relies on the interaction of three components: a photosensitizer compound, oxygen within the tissues and light having properties suitable for activating the photosensitizer compound. The photosensitizer compound injected within the body of the patient is absorbed by all cells but remains a longer time within the tumour cells. Upon activation of the photosensitizer compound by the light, photochemical reactions occur resulting in a destruction of the tumour cells.

An example of a treatment by photodynamic therapy of a glioblastoma is disclosed by Lyons et al. in "*The effects of PDT in primary malignant brain tumours could be improved by intraoperative radiotherapy*", Photodiagnosis and Photodynamic Therapy, 2012, 9: 40-45. The known system for treatment by photodynamic therapy is of the type comprising an illuminating device intended for illuminating the cavity to be treated. The illuminating device comprises an illuminating member extending along a central axis between opposed proximal and distal ends. The illuminating member comprises:
- a core carrying a light emitting surface for emitting a light adapted to activate the photosensitizer compound, the light emitting surface being arranged at the distal end of the illuminating member, and
- a hollow sheath having a balloon arranged at the distal end of the illuminating member, the sheath being adapted to receive the core with the light emitting surface arranged within the balloon, the balloon comprising a wall which has an inner surface delimiting an internal space, and an outer surface, the wall being flexible and adapted to allow diffusion of the light emitted by the light emitting surface, the balloon presenting an inflated state in which the wall has a symmetry of revolution about the central axis and the internal space is filled with a light diffusing solution so as to diffuse the light emitted by the light emitting surface, and a deflated state in which the internal space is empty.

Examples of other known systems implementing such illuminating member are disclosed in US 2002/087206, WO 2014/145179 and by DeLaney et al. in "*A light-diffusing device for intraoperative photodynamic therapy in the peritoneal or pleural cavity*", Journal of Clinical Laser Medecine & Surgery, Octobre 1991, 361-366.

However, the known systems have not allowed to significantly improve survival. In particular, such systems cannot efficiently treat a cavity of large dimensions as it is often the case after surgical resection of glioblastoma.

The invention aims to solve the above mentioned problems.

To this end, according to a first aspect, the invention provides a system of the aforementioned type wherein the internal space of the balloon has a variable capacity, the wall of the balloon being elastically extendible and the balloon presenting a plurality of inflated states in each of which the internal space is filled with a volume of light diffusing solution, and wherein the system further comprises a support provided with a transfer function relating the volume of light diffusing solution of each inflated state with at least one of a corresponding distribution of light power at the outer surface of the wall of the balloon and a corresponding time of illumination for providing a determined dose of light energy.

Hence, the balloon can be adapted to the cavity to be treated by filling its internal space with the light diffusing solution until its wall comes in contact with tissues delimiting the cavity. The distribution of light power or the time of illumination corresponding to the volume of light diffusing solution being known, it is possible to deliver the appropriate dose of light energy in a complete and homogeneous manner. In addition, thanks to a simple and reliable control of the delivered dose of light energy offered by the invention, the treatment can be easily reproducible. The efficiency of the treatment by photodynamic therapy is thereby enhanced.

The support may comprise a display on which the transfer function is visible.

The system may further comprise an electronic unit connected to the illumination device and controlling the illumination device, especially as regards the time of illumination, as a function of the volume of light diffusing solution, the support comprising a memory of the electronic unit storing the transfer function.

The transfer function may be at least one of a table and a graph relating the volume of light diffusing solution of each inflated state with at least one of the corresponding distribution of light power at the outer surface of the wall of the balloon and the corresponding time of illumination for providing a determined dose of light energy.

The core of the illuminating member may be an optical fiber having a proximal end and a distal end which carries the light emitting surface, and the illuminating device may further comprise a laser light source connected to the proximal end of the optical fiber.

The sheath may include:
- a trocar device comprising a balloon shaft that is tubular along the central axis and that has a proximal end and a distal end provided with the balloon,
- a guide tubular about the central axis and comprising a transparent end portion provided with a transverse end surface, the guide being adapted to be inserted within the trocar device with the transparent end portion arranged within the balloon, and a locking device adapted to lock the optical fiber inserted within the guide with the distal end of the optical fiber being arranged within the transparent end portion of the guide in abutment against the transverse end surface.

Thanks to these provisions, the optical fiber can be accurately positioned in a reproducible manner.

The light emitting surface may extend along the central axis and be adapted to emit the light transversely with respect to the central axis.

The light emitting surface may have a length between 15 mm and 70 mm.

The capacity of the internal space of the balloon may vary from 30 ml to 500 ml.

According to a second aspect, the invention provides a method for preparation of a system for treatment as previously defined, the method for preparation comprising repeatedly performing steps of:

filling the internal space of the balloon with a volume of light diffusing solution, and measuring at least one of a corresponding distribution of light power at the outer surface of the wall of the balloon and a corresponding time of illumination for providing a determined dose of light energy.

The method may further comprise performing a step of measuring a corresponding time of illumination for providing a determined dose of light energy after each step of measuring the corresponding distribution of light power.

The system as previously defined may be implemented in a method for treatment by photodynamic therapy of a cavity of a patient's body, the method comprising the steps of:

placing the balloon in the deflated state in the cavity, conforming the balloon to the cavity, the internal space of the balloon being filled with a volume of light diffusing solution so that the wall of the balloon comes in contact with tissues delimiting the cavity, activating the photosensitizer, the cavity being illuminated by the light emitting surface arranged in the balloon as a function of the volume of light diffusing solution with which the internal space of the balloon is filled.

In the method for treatment by photodynamic therapy, the step of activating the photosensitizer may be performed for a time of illumination determined as a function of the volume of light diffusing solution with which the internal space of the balloon is filled.

Figure 2:
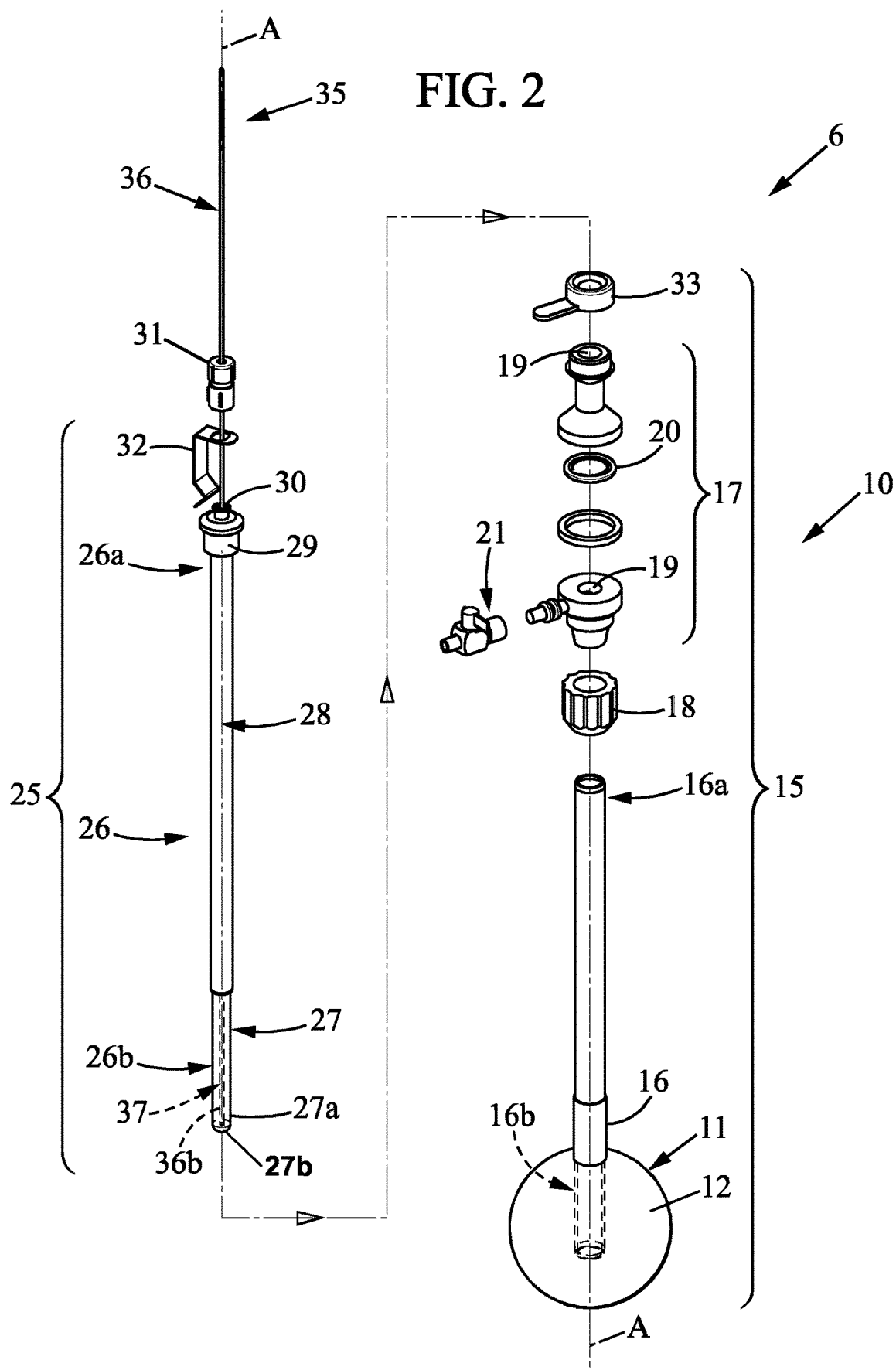
Figure 3:
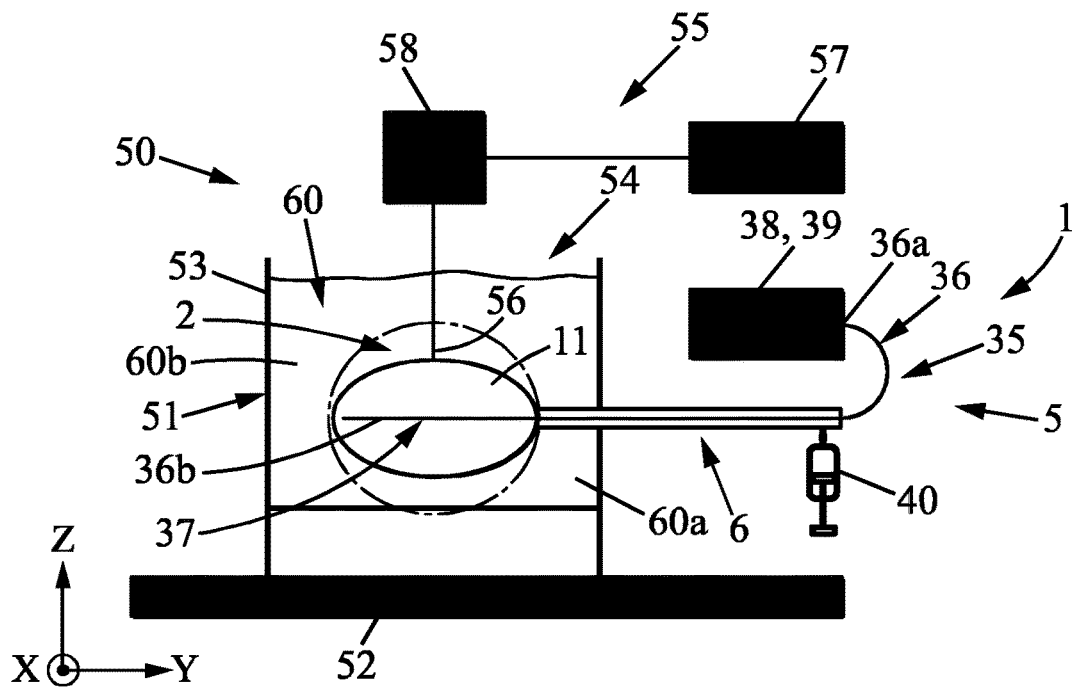
Figure 4:
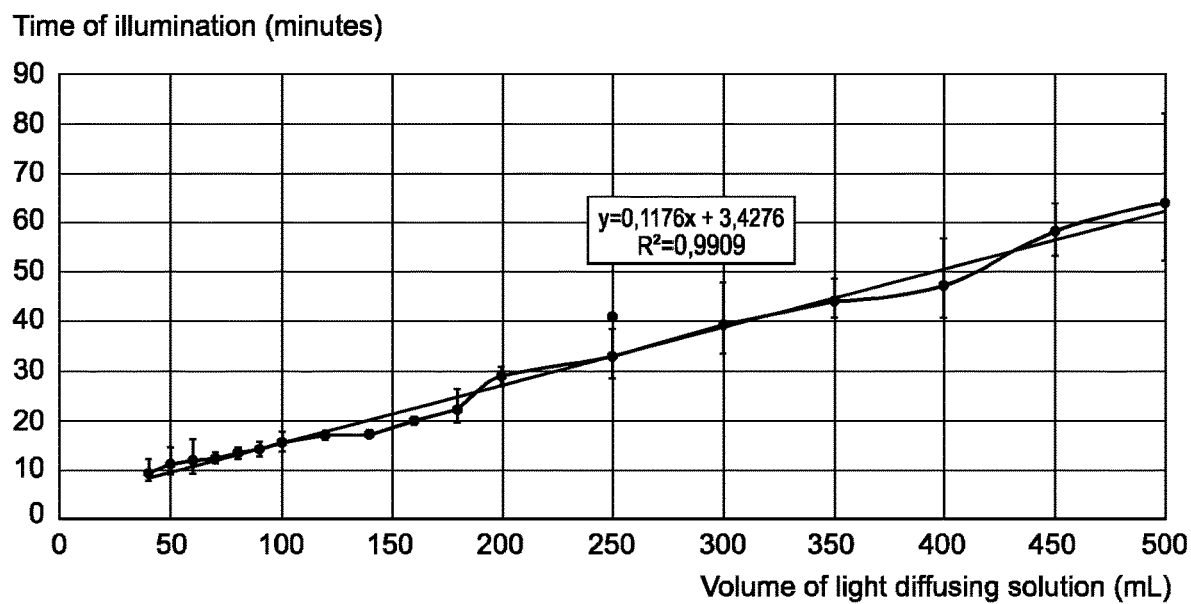
Figure 5:
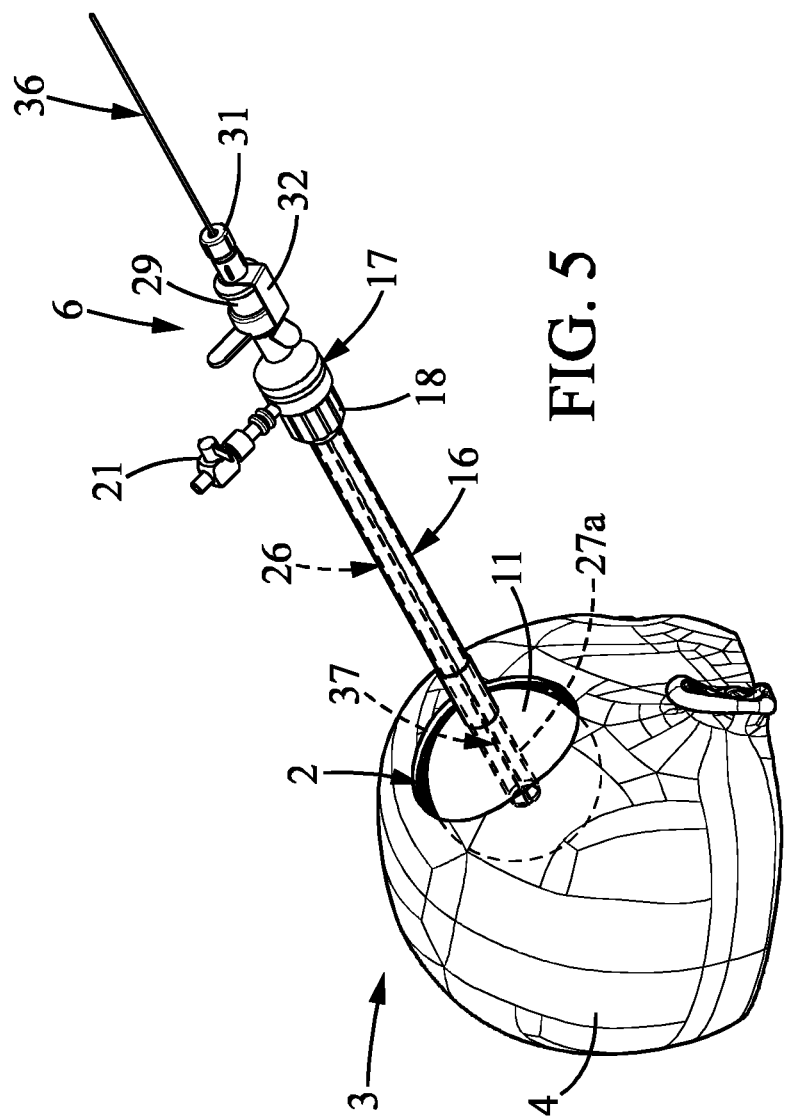

Other objects and advantages of the invention will emerge from the following disclosure of a particular embodiment of the invention given as non limitative example, the disclosure being made in reference to the enclosed drawings in which:

FIG. 1 is a perspective view of an illuminating member of a system for treatment by photodynamic therapy of a cavity of a patient's body according to an embodiment of the invention, the illuminating member having a distal end provided with a balloon and a light emitting surface arranged within the balloon, the balloon has a variable capacity and can be filled with different volumes of a light diffusing solution, each volume of light diffusing solution being related with a corresponding distribution of light power at an outer surface of the balloon, FIG. 2 is an exploded view of the illuminating member of FIG. 1, FIG. 3 is a schematic view illustrating the system with the illumination member of FIG. 1 arranged on a test bench for measuring the distribution of light power at the outer surface of the balloon corresponding to each volume of light diffusing solution, FIG. 4 is a graph illustrating an illumination time as a function of the volume of light diffusing solution resulting from measurements performed with the test bench of FIG. 3, FIG. 5 is a perspective view of a step of a method for treatment by photodynamic therapy of a cavity implementing the illuminating member of FIG. 1, the cavity resulting from surgical resection of a glioblastoma.

On the Figures, the same reference numbers refer to the same or similar elements.

Figures illustrate a system 1 for treatment by photodynamic therapy of a cavity 2 of a patient's body 3. In a particular non-limitative example disclosed in details in relation with FIG. 5, the system 1 is applied to the treatment of a cavity 2 in the patient's head 4 resulting from surgical resection of a glioblastoma.

The photodynamic therapy (PDT) relies upon activation of a photosensitizer compound, previously injected within the body 3 of the patient and absorbed by cells, by a suitable light to destroy tumorous cells in which the photosensitizer compound is preferentially accumulated.

The system 1 comprises an illuminating device 5, schematically shown on FIG. 3, for illuminating the cavity to be treated with a light adapted to activate the photosensitizer compound.

The illuminating device 5 comprises an illuminating member 6, shown on FIGS. 1 and 2, adapted to be manipulated by an operator, human or robotized.

The illuminating member 6 extends along a central axis A between opposed proximal 6a and distal 6b ends. In the illustrated embodiment, the central axis A is straight between the proximal 6a and distal 6b ends to ease its manipulation, although it could present one or more curvatures depending on the application. The illuminating member 6 comprises a handling part 7 extending from the proximal end 6a of the illuminating member 6 and a light diffusing part 8 arranged at the distal end 6b of the illuminating member 6.

The illuminating member 6 comprises a biocompatible hollow sheath 10, for example tubular of circular cross-section, centered on the central axis A, and a core 35 carrying a light emitting surface 37 for emitting light adapted to activate the photosensitizer compound.

The sheath 10 presents has an overall rigidity over the handling part 7 to further ease manipulation of the illuminating member 6. At the light diffusing part 8 of the illuminating member 6, the sheath 10 comprises a balloon 11 intended to centrally receive the light emitting surface 37. The balloon 11 is further intended to be filled with a light diffusing solution adapted to diffuse the light emitted by the light emitting surface 37.

The balloon 11 comprises a wall 12 which has an inner surface delimiting an internal space, and an outer surface. The wall 12 of the balloon 11 is made of material allowing diffusion of the light emitted by the light emitting surface 37, especially a transparent or translucent material. The wall 12 of the balloon 11 is also flexible and elastically extendible. The balloon 11, for example made of silicone, presents a deflated state in which the internal space is empty. It may also present a plurality of inflated states in each of which the wall 12 has a symmetry of revolution about the central axis A and the internal space may be filled with a volume of light diffusing solution. In a particular example, the internal space has a capacity that varies from 30 ml to 500 ml.

As shown on FIG. 2, in the illustrated embodiment, the sheath 10 combines a trocar device 15 and a guide device 25.

The trocar device 15 may be of the type of the device exploited by the company Aesculap® AG under the name Herloon®. The trocar device 15 comprises a balloon shaft 16 made of silicone and extending between a proximal end 16a and a distal end 16b which is provided with the balloon 11. The trocar device 15 further comprises a trocar body 17 connected to the proximal end 16a of the balloon shaft 16 through a fitting assembly 18. The trocar body 17 includes a through internal passage 19 in communication with an interior of the balloon shaft 16. The trocar body 17 is provided with a flap valve 20 to selectively close or open the internal passage 19 while ensuring its tightness. The trocar body 17 also comprises a shut-off cock 21 opening in the internal passage 19. The shut-off cock 21 is connectable to an external device, such as a pump for example of manual type or a syringe 37, adapted to fill the balloon 11 with a fluid and/or remove a fluid from the balloon 11.

The guide device 25 comprises a tubular guide 26 extending between proximal 26a and distal 26b ends, and a trocar adaptor 29 connected to the proximal end 26a of the guide 26. The guide 26 presents an overall rigidity and has at least a transparent end portion 27a at its distal end 26b. In the illustrated embodiment, the guide 26 comprises a first tube 27 made of transparent material, such as glass, coaxially fitted in a second tube 28, for example made of metal such as stainless steel. The first tube 27 is longer than the second tube 28 so that once the first 27 and second 28 tubes are secured to the trocar adaptor 29, the end portion 27a of the first tube 27 protrudes from the second tube 28. The end portion 27a extends over a sufficient length for housing the light emitting surface 37 and has a transverse end surface 27b perpendicular to the central axis A. The trocar adaptor 29 comprises a trough internal passage 30 in communication with an interior of the guide 26. The trocar adaptor 27 is also provided with a locking device 31, for example of Luer type, for locking the core 35 inserted within the guide 26 through the internal passage 30 of the trocar adaptor 29.

The guide device 25 is assembled to the trocar device 15 with the guide 16 of the guide device 25 inserted in the balloon shaft 16 of the trocar device 15 through the internal passage 19 of the trocar body 17 until the transparent end portion 27a of the guide device 25 is arranged within the balloon 11 of the trocar device 15 and the trocar adaptor 29 of the guide device 25 rests on a top end surface the trocar body 17. To maintain the guide 25 and trocar 15 devices in an assembled state and ensure tightness, a spring tab 32 urges the trocar adaptor 29 against the top end surface of the trocar body 17 with interposition of a sealing cap 33, for example made of silicone, between them.

The core 35 is an optical fiber 36 having a proximal end 36a and a distal end 36b which carries the light emitting surface 37. In the illustrated embodiment, the light emitting surface 37 is arranged along a portion of a lateral surface extending around an axis of the optical fiber 36 so that light may be emitted transversely with respect to axis of the optical fiber 36. To illuminate large cavities, the light emitting surface 37 may have a length between 15 mm and 70 mm and a core diameter between 250 µm and 750 mm. In a particular non-limitative example, the optical fiber 36 of the type of the optical fiber exploited by the company Medlight S.A. under the reference RD-ML 70 mm, the light emitting surface 37 of which is 70 mm in length and 500 µm in diameter. In a variant, the core may be of any other suitable type and especially any kind of optical fiber.

The optical fiber 36 may be inserted in the sheath 10 along the central axis A until the light emitting surface 37 is arranged within the transparent end portion 27a of the guide device 25 of the sheath 10 in abutment with the transverse end surface 27b so that the light emitting surface 37 is centered on the central axis A and accurately positioned within the balloon 11 of the trocar device 15 of the sheath 10, to emit light transversely with respect to the central axis A. Once inserted, the optical fiber 36 may be locked in place by the locking device 31 of the trocar adaptor 29.

The illuminating device 5 further comprises a light source 38 and, in particular a laser light source, connected to the proximal end 36a of the optical fiber 36 and adapted to generate the light at determined wavelength and power so as to activate the photosensitizer compound. In a particular non-limitative example, the light source 38 is a laser light source of the type of the laser exploited by the company Biolitec AG under the reference Ceralas D50, implementing a LED technology at a wavelength of 630±3 nm, with a maximum power of 3 W.

According to the invention, a support is provided with a transfer function relating the volume of light diffusing solution of each inflated state with a corresponding distribution of light power at the outer surface of the wall 12 of the balloon 11 and/or a corresponding time of illumination for providing a determined dose of light energy. In particular, as shown on FIG. 4, the transfer function may be a graph relating each volume of light diffusing solution with a corresponding time of illumination for providing a determined dose of light energy. In a variant, the transfer function may be a table.

The support may comprise a display on which the transfer function is visible by the operator manipulating the illuminating member. The display may be a sheet on which the transfer function is printed. In a variant, the display may be electronic such as a screen of a computer on which the transfer function is displayed.

The time of illumination may be manually controlled by the operator on the basis of the transfer function associating each value of a range of volumes of light diffusing solution to at least one of:
  a set of values of light power at the outer surface of the wall 12 of the balloon 11, and
  a time of illumination for providing the determined dose of light energy.

In a variant, the time of illumination may be automatically controlled. To that end, the system 1 may comprise an electronic unit 39 having a memory as support on which the transfer function is stored. The electronic unit 39 is connected to the illumination device 5 and controls the illumination device 5, and especially the light source 38, on the basis of the transfer function stored in the memory. The electronic unit 39 may be integral with light source 38 or separate from it. The electronic unit 39 may then monitor in real-time the dose of light energy delivered to the tissues delimiting the cavity 2.

FIGS. 3 and 4 illustrate a method for preparation of the system 1 enabling, in particular, the transfer function to be built.

A test bench 50 for measuring the distribution of light power at the outer surface of the wall 12 of the balloon 11 corresponding to each volume of light diffusing solution is represented on FIG. 3.

The test bench 50 comprises a container 51 with a bottom 52, an opaque, in particular black, lateral wall 53 and an open top 54. The test bench 50 also comprises a measuring system 55 made of:

an isotropic sensor 56, for example of the type of the sensor exploited by the company Medlight under the reference Isoprobe IP85, a wattmeter 57 connected to the isotropic sensor 56, for example of the type of the wattmeter exploited by the company Newport under the reference 1918-R, and a support 58 enabling the isotropic sensor 56 to be arranged at different locations within the container 51.

A biological material provided with a cavity 2 is used. In particular, the biological material may be a brain 60. The brain 60 is cut in two halves and the cerebellum, the brain stem and corpus callosum are extracted. Each half of the brain 60 is slit in a longitudinal direction in order to expose internal tissues (gray and white matters) to the illuminating member 6.

The light diffusing solution is prepared. In particular, a light diffusing solution of a concentration of 0.1% is prepared by injecting 5 mL of intralipid liquid, such as an intralipid liquid with a concentration of 20% exploited by the company Fresenius Kabi France, in 1 L of physiological serum to form a mixture that is agitated until an homogeneous solution is obtained.

A first half 60a of the brain 60 is disposed on the bottom 52 of the container 51. The balloon 11 of the illuminating member 6 in the deflated state is inserted in the container 51 above the first half 60a of the brain 60. The laser source 38 is switched on and the optical fiber 36 is calibrated. The optical fiber 36 is then inserted within the sheath 10 of the illuminating member 6 and locked to it by the locking device 31 of the trocar adaptor 29 once the light emitting surface 37 is arranged in the balloon 11. The second half 60b of the brain 60 is disposed on the balloon 11 of the illuminating member 6.

The internal space of the balloon 11 is filled with a volume of light diffusing solution through the shut-off cock 21 for example by means of a syringe 40. It should be noted that before filling the balloon 11 with the light diffusing solution, it may be ensured that the internal space of the balloon 11 is emptied. A pump, for example of manual type, may be connected to the shut-off cock 21.

For the volume of light diffusing solution, a corresponding distribution of light power at the outer surface of the wall 12 of the balloon 11 may be measured by moving the isotropic sensor 56 to different locations of the outer surface of the wall 12 of the balloon 11. Thanks to these measurements, irradiance of the illuminating member 6 may be calculated and thereby the time of illumination for providing the determined dose of light energy corresponding to the volume of light diffusing solution may be determined.

The volume may then be varied, for example in an incremental manner, by adding successively additional volumes of the light diffusing solution. The measurements are performed after each addition of additional volume to have the distribution of light power at the outer surface of the wall 12 of the balloon 11 and the time of illumination for providing the determined dose of light energy corresponding to each volume of light diffusing solution.

As shown on FIG. 4, a graph illustrating the time of illumination as a function of the volume of light diffusing solution resulting from the measurements performed with the test bench 50 of FIG. 3 can be obtained.

A method for treatment by photodynamic therapy of a cavity 2 of a patient's body 3 is now disclosed in relation with FIG. 5 which illustrates a cavity 2 in the patient's head 4 resulting from surgical resection of a glioblastoma.

The treatment by photodynamic therapy is intraoperative and performed after an exeresis of the glioblastoma. In particular, during the neurosurgical procedure of exeresis of the glioblastoma, a contrast agent may be injected in the tissues to enable the neurosurgeon to perform a visual prognostic of the tumor inside the cavity 2. The contrast agent may be a medicine exploited by the company Medac GmbH under the name Gliolan®, which is known to be more selective than many other contrast agents. A substance deriving from the metabolization of the contrast agent may be absorbed within the tissues delimiting the cavity 2 and used as the photosensitizer for the photodynamic therapy.

Components of the illuminating member 6 are gathered. These components have been previously sterilized for those which can be reusable or sterile for those which may be not reusable. In a non-limitative example, the optical fiber 36 and the trocar body 17 of the trocar device 15 of the sheath 10 may be reusable and sterilized while the balloon shaft 16 of the trocar device 15 of the sheath 10 and the guide device 25 may be sterile and disposable. In other examples, the guide device 25 could be reusable and sterilizable.

The sheath 10 of the illuminating member 6 is assembled as previously disclosed and the balloon 11 is emptied by connecting a pump, for example of manual type, to the shut-off cock 21.

The illuminating member 6 is held by the operator, human or robotized, and moved towards the cavity 2 so that the balloon 11 in the deflated state is placed in a center of the cavity 2.

The balloon 11 is conformed to the cavity 2 by filling its internal space through the shut-off cock 21 with successive known volumes of the previously disclosed intralipid solution as light diffusing solution until the wall 12 of the balloon 11 comes in contact with tissues delimiting the cavity 2.

The total volume of light diffusing solution is noted.

The optical fiber 36 is connected to the laser light source 38 and, once calibrated if necessary, inserted in the guide device 25 of the sheath 10 until the light emitting surface 37 reaches the transparent end portion 27a. The light emitting surface 37 is centrally arranged in the balloon 11 and the optical fiber 36 is locked in place by the locking device 31 of the trocar adaptor 29.

The time of illumination is determined based on the volume of light diffusing solution with which the balloon 11 has been filled.

The electronic unit 39, for example integral with the laser light source 38, is set with the power, such as 2 W, and the determined time of illumination.

The cavity 2 is illuminated by the light emitting surface 37 arranged in the balloon 11 in accordance with settings of the light source 38. Time of illumination is controlled according to the transfer function either manually or through the electronic unit 39 to activate the photosensitizer and induce a localized therapeutic effect.

The invention claimed is:

1. System for treatment by photodynamic therapy of a cavity of a patient's body, the cavity being delimited by tissues comprising cells having a photosensitizer compound absorbed therein, the system comprising an illuminating device intended for illuminating the cavity to be treated, wherein the illuminating device comprises an illuminating member extending along a central axis between opposed proximal and distal ends, the illuminating member comprising:

a core carrying a light emitting surface for emitting a light adapted to activate the photosensitizer compound, the light emitting surface being arranged at the distal end of the illuminating member, a hollow sheath having a single balloon arranged at the distal end of the illuminating member, the hollow sheath being adapted to receive the core with the light emitting surface arranged within the balloon, the balloon comprising a wall which has an inner surface delimiting an internal space, and an outer surface, the wall being flexible and adapted to allow diffusion of the light emitted by the light emitting surface, the balloon presenting at least one inflated state in which the wall has a symmetry of revolution about the central axis, and the internal space is filled with a light diffusing solution so as to diffuse the light emitted by the light emitting surface, and a deflated state in which the internal space is empty, wherein the internal space of the balloon has a variable capacity, the wall of the balloon being elastically extendible and the balloon presenting a plurality of inflated states in each of which the internal space is filled with a volume of light diffusing solution, and an electronic unit connected to the illumination device and controlling the illumination device as a function of the volume of light diffusing solution, wherein the system further comprises a support provided with a transfer function relating the volume of light diffusing solution of each inflated state with at least one of a corresponding distribution of light power at the outer surface of the wall of the balloon and a corresponding time of illumination for providing a determined dose of light energy such that the system is configured to measure at least one of the corresponding distribution of light power at the outer surface of the wall of the balloon and the corresponding time of illumination for providing the determined dose of light energy at the plurality of inflated states of the single balloon, the support comprising a memory of the electronic unit storing the transfer function, the support comprising a memory of the electronic unit storing the transfer function.

2. System according to claim 1, wherein the support comprises a display on which the transfer function is visible.

3. System according to claim 1, wherein the transfer function is at least one of a table and a graph relating the volume of light diffusing solution of each inflated state with at least one of the corresponding distributions of light power at the outer surface of the wall of the balloon and the corresponding time of illumination for providing the determined dose of light energy.

4. System according to claim 1, wherein the core of the illuminating member is an optical fiber having a proximal end and a distal end which carries the light emitting surface, and wherein the illuminating device further comprises a laser light source connected to the proximal end of the optical fiber.

5. System according to claim 4, wherein the sheath includes:
   a trocar device comprising a balloon shaft that is tubular along the central axis and that has a proximal end and a distal end provided with the balloon,
   a guide tubular about the central axis and comprising a transparent end portion provided with a transverse end surface, the guide being adapted to be inserted within the trocar device with the transparent end portion arranged within the balloon, and
   a locking device adapted to lock the optical fiber inserted within the guide with the distal end of the optical fiber being arranged within the transparent end portion of the guide in abutment against the transverse end surface.

6. System according to claim 1, wherein the light emitting surface extends along the central axis and is adapted to emit the light transversely with respect to the central axis.

7. System according to claim 6, wherein the light emitting surface has a length between 15 mm and 70 mm.

8. System according to claim 1, wherein the capacity of the internal space of the balloon varies from 30 ml to 500 ml.

9. Method for preparation of a system for treatment according to claim 1, the method for preparation comprising repeatedly performing steps of:
   filling the internal space of the balloon with the volume of light diffusing solution, and
   measuring at least one of the corresponding distribution of light power at the outer surface of the wall of the balloon and the corresponding time of illumination for providing the determined dose of light energy,
wherein the volume of light diffusing solution is varied such that the measuring step is performed at a plurality of inflated states of the balloon.

10. The method of claim 9, wherein the measuring step is performed at a plurality of inflates states of the balloon within a single cavity.

\* \* \* \* \*